(12) United States Patent
Besch et al.

(10) Patent No.: US 6,356,617 B1
(45) Date of Patent: Mar. 12, 2002

(54) DEVICE FOR DIGITAL SUBTRACTION ANGIOGRAPHY

(75) Inventors: Hans Jürgen Besch, Netphen; Michael Lohmann, Hamburg, both of (DE)

(73) Assignee: Deutsches Elektronon-Synchrotron DESY, Hamburg (DE)

( * ) Notice: Subject to any disclaimer, the term of this patent is extended or adjusted under 35 U.S.C. 154(b) by 0 days.

(21) Appl. No.: 09/582,063

(22) PCT Filed: Dec. 14, 1998

(86) PCT No.: PCT/EP98/08037

§ 371 Date: Sep. 5, 2000

§ 102(e) Date: Sep. 5, 2000

(87) PCT Pub. No.: WO99/32901

PCT Pub. Date: Jul. 1, 1999

(30) Foreign Application Priority Data

Dec. 22, 1997 (DE) .......................... 197 58 363

(51) Int. Cl.⁷ .......................... H05G 1/64; G01T 1/185
(52) U.S. Cl. .................... 378/98.11; 250/385.1
(58) Field of Search .................... 378/84, 85, 98.11, 378/156, 157, 158, 160, 208; 250/385.1

(56) References Cited

U.S. PATENT DOCUMENTS

| 4,535,245 A | * | 8/1985 | Zonnevald et al. | ...... 250/385.1 |
| 4,736,398 A | * | 4/1988 | Graeff et al. | .............. 378/98.3 |
| 4,780,897 A | * | 10/1988 | McDaniel et al. | ........... 378/62 |
| 4,973,846 A | * | 11/1990 | Lanza et al. | ............. 250/385.1 |
| 5,508,526 A | * | 4/1996 | Labbe | ........................ 250/374 |

OTHER PUBLICATIONS

Ultra–low bias current Difet® operational amplifier (OPA129 data sheet), Bur–Brown Corporation (Jul. 1994).*

* cited by examiner

Primary Examiner—Robert H. Kim
Assistant Examiner—Allen C. Ho
(74) Attorney, Agent, or Firm—Foley & Lardner

(57) ABSTRACT

The invention relates to a device for digital subtraction angiography in an energy subtraction mode with a special electronic circuit.

14 Claims, 3 Drawing Sheets

DEVICE FOR DIGITAL SUBTRACTION ANGIOGRAPHY

Figure 1:
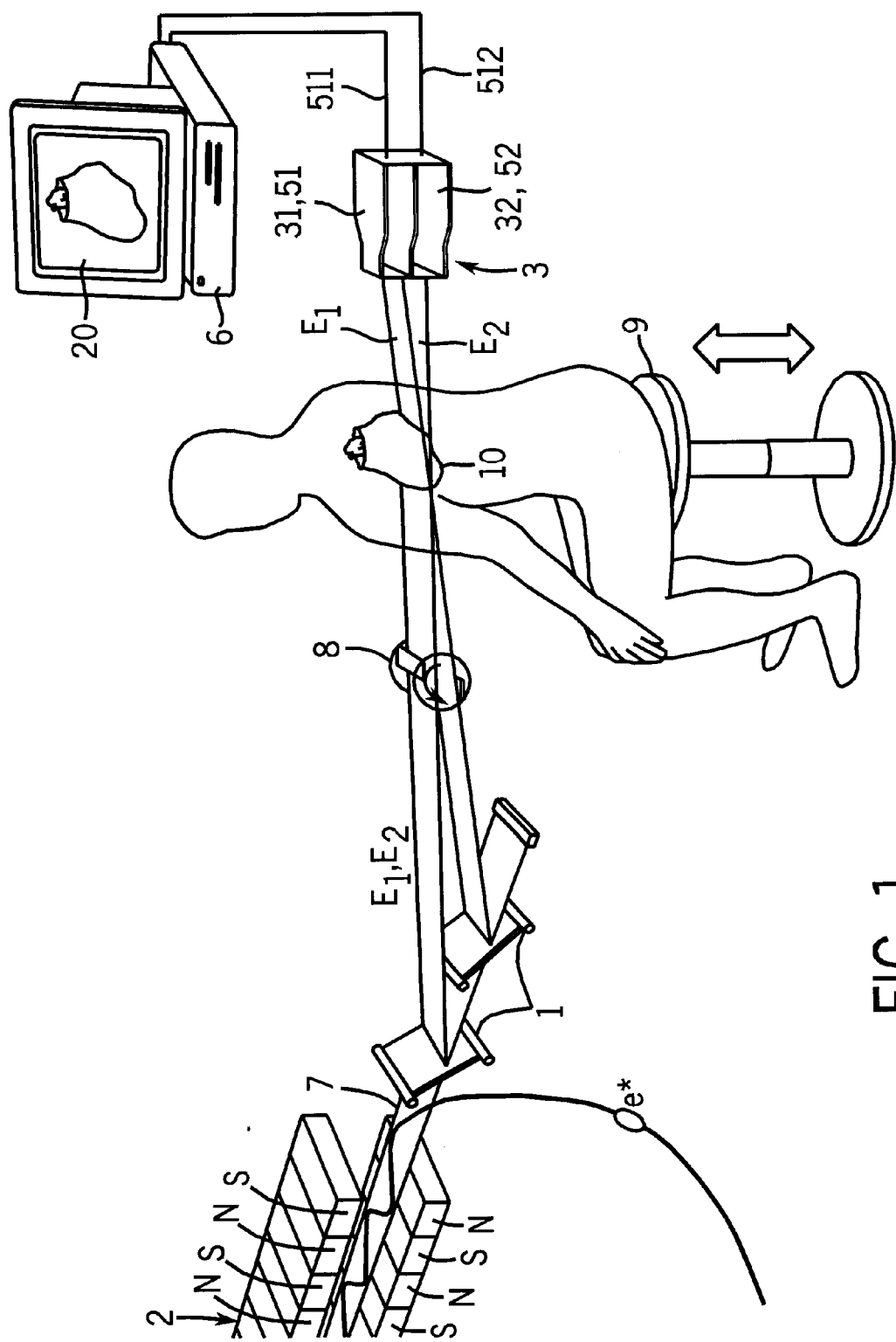

The invention relates to a device according to the characterizing part of patent claim 1.

Such a device is already known from DE 35 17 101 C1. It is used for examination of the heart with the aim of establishing whether an acute blockage of a coronary vessel by a blood clot is to be feared. For this purpose, an iodine contrast medium is injected into an arm vein of the patient and the patient is irradiated line-by-line simultaneously with two linearly collimated X-ray beams, of which one has an energy $E_1$ just below the iodine absorption edge of 33 keV and the other has an energy $E_2$ just above the iodine absorption edge. The two X-ray beams are focussed on the heart of a patient and impinge behind it on a detector with two counting chambers arranged parallel to one another at a distance, the signals of which are converted via a charge-sensitive A/D converter into digital signals and transmitted to a computer, which then composes in each case an image of the energy $E_1$ and an image of the energy $E_2$ and subtracts the images from one another logarithmically. It displays the resulting image on a monitor.

DE 39 01 837 A1 discloses a radiation detector which is capable of measuring the local distribution of high beam intensities with a high accuracy, a wide dynamic range and high sensitivity in short recording times. Applications lie, for example, in medical diagnostics for instantaneous recording of rapidly moved parts (coronary vessels). Pulsed radiation sources are used for this, the signals of the individual quanta which belong to a beam pulse being totalled in a proportional chamber and these individual signals per radiation source pulse thus obtained either already representing the required intensity signal or being totalled up electronically per image point over a number of radiation source pulses. DE 39 01 837 A1 furthermore provides the construction of such a detector. However, the disadvantage of this detector is that, together with conventional amplifier and converter circuits, the required image resolution cannot be achieved.

The object of the invention is to improve the device of the abovementioned type to the extent that the resolution of the resulting image is better, so that coronary vessels in particular can be shown more clearly.

This object is achieved by a device with the features of patent claim 1.

It comprises a high-sensitivity amplifier and analogue-digital converter with very high dynamics, with which the high absorption differences in iodine-filled bodies can be shown in linear form. In this way it is possible to show all three coronary vessels in spite of overlapping by iodine-filled ventricles.

In this connection it is pointed out that imaging of the coronary vessels is so difficult because on the one hand the heart is permanently moving, and on the other hand the contrast medium enters both the ventricles and the coronary vessels.

To achieve the object described it was therefore necessary to discover for the electronic circuits used a suitable component in the form of a current- or charge-digital converter which has a dynamic range of at least 18 bits, in order to achieve a sufficiently good resolution in the form of differences in colour or contrast.

Figure 2:
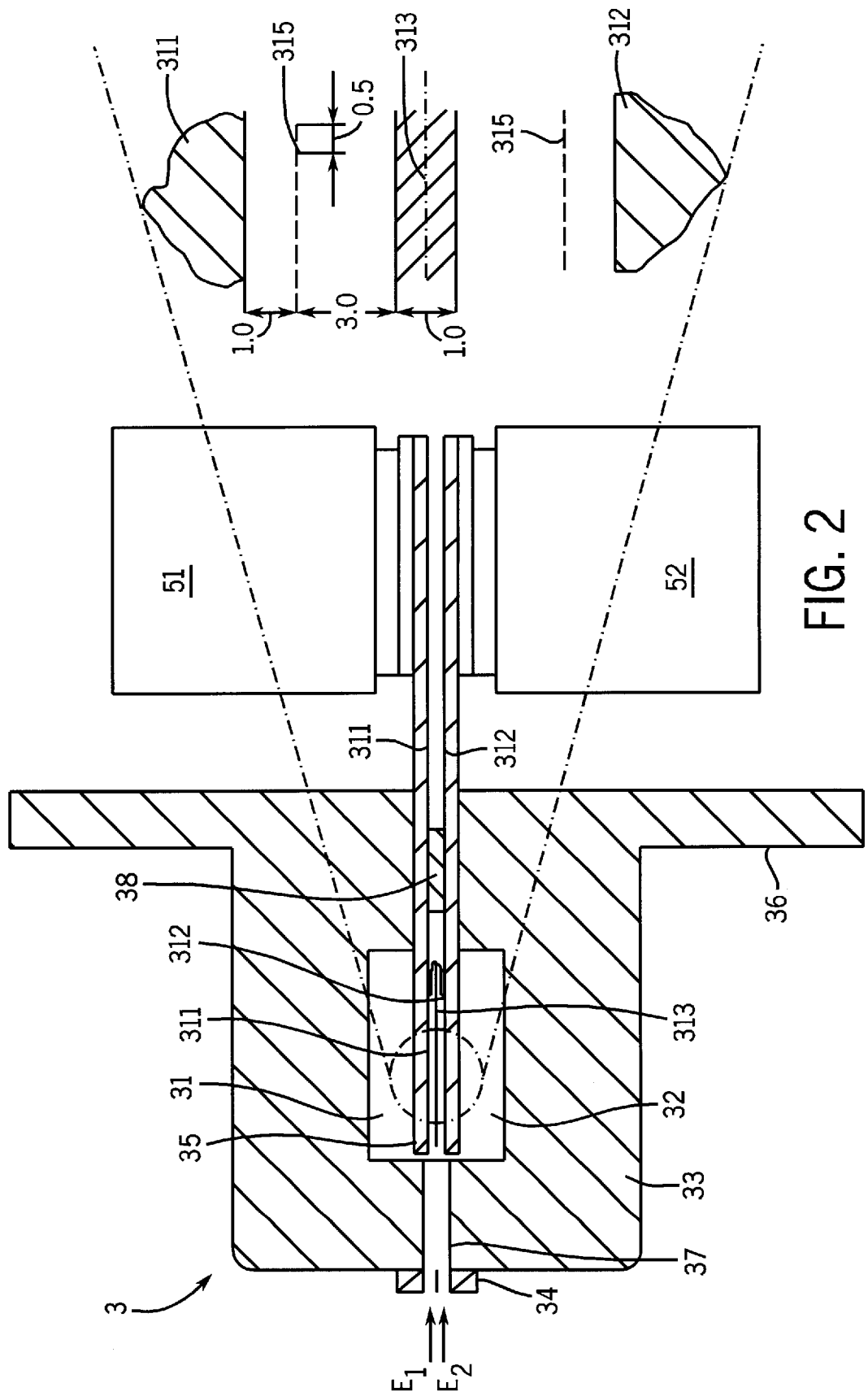
Figure 3:
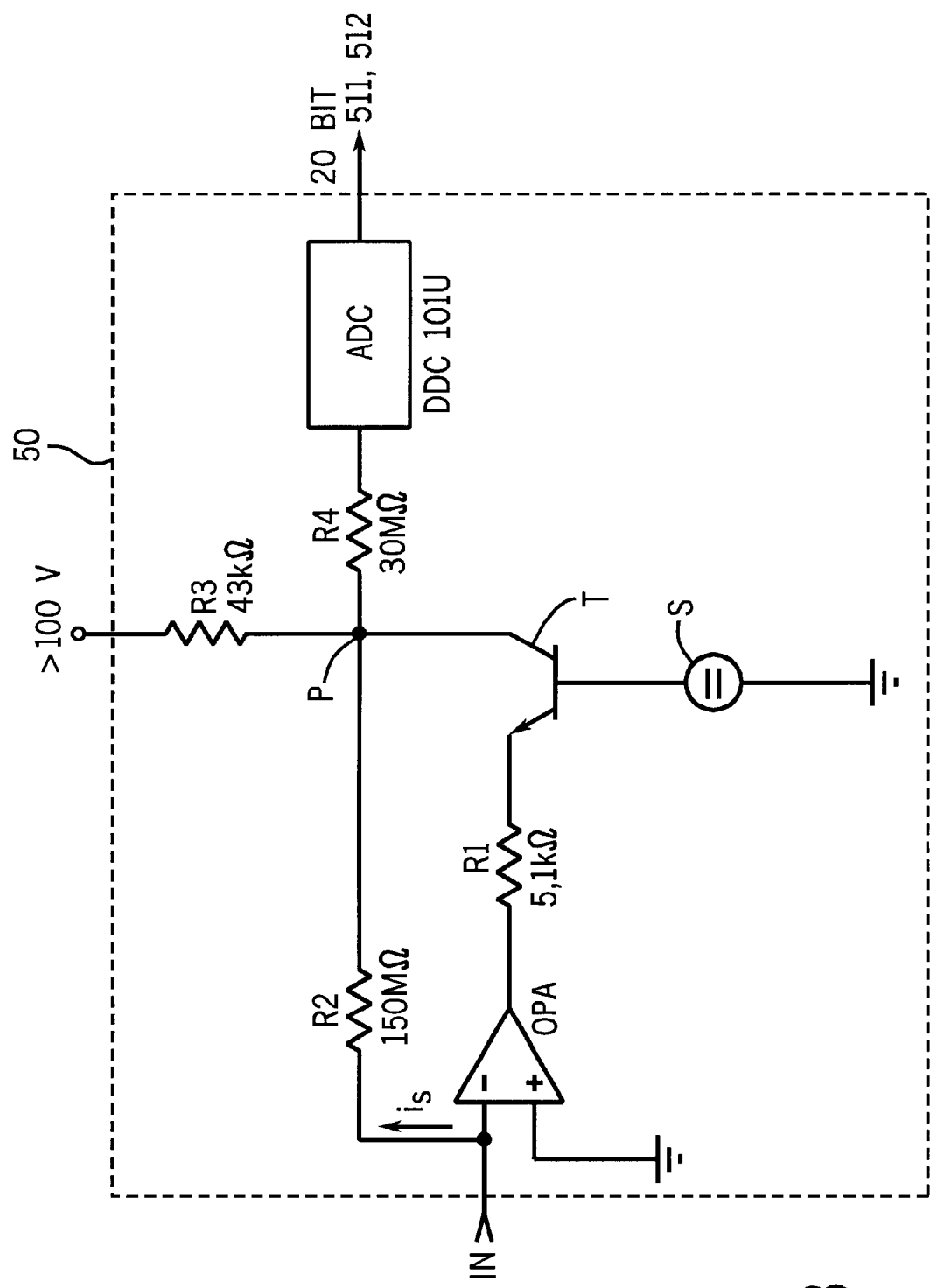

The invention is explained in the following in more detail with the aid of figures; where FIG. 1 shows a device in diagram form of the device in the beam path of the X-radiation of a synchrotron;

FIG. 2 shows a side view in diagram form of the detector used in the device according to FIG. 1; and FIG. 3 shows a circuit diagram of an electronic circuit used in the detector from FIGS. 1 and 2.

FIG. 1 shows as the source of X-radiation, for example, a storage ring such as is available as DORIS from the Applicant. In this, the spinning positron beam $e^+$ is deflected backwards and forwards in a plane between the poles of a so-called wiggler magnet approximately in the manner shown by pairs of poles which are each connected in series but are of reverse polarity, which leads to an intense formation of synchrotron radiation. This synchrotron radiation is a polychromatic or "white" beam 7, which is passed through a system, not shown, of collimators and diaphragms on to a monochromator 1. In the case of DORIS, the monochromator 1 is about 15 to 36 m away from the wiggler magnet 2, which forms the source point of the radiation. In the vicinity of its source point the "white" beam 7 has an approximately elliptical cross-section, the small axis of which is about 2 mm long, while the length of the horizontally lying large axis is about 4 mm. Due to beam diaphragms and natural divergence, the beam 7 has a horizontal width of approximately 100 mm and a height of approximately 2.5 mm at the location of the monochromator 1. By using a double monochromator 1, two monochromatic beams with an energy of $E_1$ and $E_2$ are formed therefrom. The monochromatic beams $E_1$ and $E_2$ arrive at the input of a detector 3, passing through the heart 10 of a patient on their route during operation. At the input of the detector 3 they have a separation of 1.5 mm and a horizontal width of currently 120 mm, and in each case a height of 1.0 mm.

The detector 3 has two ionization chambers 31, 32 with connected detection circuits 51, 52. The output signals from the detection circuits 51, 52 of the detector 3 are transmitted via leads 511, 512 to a computer system 6 which controls the image evaluation in a manner known per se, for example in accordance with DE 35 17 101 C1, by subtracting in each case an image of the energy $E_1$ from a second image of the energy $E_2$ and displaying the resulting image on a monitor 20.

During operation of the device according to the invention, a patient sits on a stool 9 which can be moved upwards and downwards in a controlled manner by a hydraulics system. This movement is indicated by the double arrow. In one embodiment, the stool 9 carries out an upwards movement of about 40 cm, the first 10 cm being for acceleration of the stool 9 and the patient sitting on it, the subsequent 20 cm of its path being for movement at a constant speed of 50 cm/sec, and the last 10 cm being for braking. As a result, the patient's organ to be examined, for example the heart 10, moves through the two monochromatic beams $E_1$ and $E_2$ within a period of 250 msec. One and the same examination location is thereby imaged so rapidly in succession with the beam $E_1$ and the beam $E_2$ that the two beam images can easily be subtracted in the computer system 6.

According to FIG. 1, in the beam path of the two X-ray beams between the monochromator 1 and the detector 3, still before the intersection of the two beams $E_1$, $E_2$ and therefore before the heart 10 to be examined, is provided a safety system 8 which has very rapid beam shutters which can block the X-ray beams $E_1$ and $E_2$ in less than 10 msec. Such safety systems have been employed for many years during operation of our synchrotron.

The stool 9 is also controlled via the computer system 6, without this being indicated separately in the drawing. However, controlling the hydraulics system, not shown, for raising and lowering the stool 9 from the computer system 6 presents no difficulties to the person skilled in the art.

FIG. 2 shows a vertical section through the detector 3 of FIG. 1, which is formed from two ionization chambers 31, 32 each with a plate bar 311 and 312 and a common drift cathode 313.

The two ionization chambers 31, 32 are enclosed by a housing 33 which is substantially rectangular and has a fixing flange 36 on one side. An inlet channel 37 about 10 mm high, 150 mm wide and about 30 mm long passes through the wall of the housing 33 and carries on its free end a collimator 34 which is known per se, through which the two beams $E_1$ and $E_2$ can enter. The inner end of the channel 37 is closed by a carbon fibre window (35).

Inside the housing 33 is a hollow space filled with an ionization gas, such as krypton or xenon, and a quenching gas, e.g. carbon dioxide, under a pressure of 10 to 20 bar. The partial pressure ratio of the ionization gas to quenching gas is about 90:10.

As already mentioned, each ionization chamber 31, 32 has a glass fibre-reinforced plate bar 311, 312 arranged at a distance of about 9 mm from one another. On the sides of the plate bars 311, 312 facing each other are arranged gold-plated copper strips as anode strips, which run in the beam direction and are arranged in a grid of 400 um. In the right-hand part of FIG. 2 the part of the plate bars 311, 312 emphasized by a dot-dash circle is shown in magnification. It can be seen from this that a common drift cathode 313 is arranged between the plate bars 311, 312 carrying the anode strips, and that a so-called "Frish grid", which lies closer to the plate bars 311, 312, is arranged in the space from the drift cathode 313 to the first and second plate bars 311, 312. In one embodiment the drift cathode 313 has a thickness of 1.0 mm, while the distance between the drift cathode 313 and each plate bar 311, 312 is 4.0 mm. The two Frisch grids 315 are then arranged at a distance of 1.0 mm from the plate bars 311, 312 and therefore at a distance in each case 3.0 mm from the surface of the dirt cathode 313. Frisch grids are made of special wires at a distance of 0.5 mm, which shield the ions formed in the ionization chambers 31, 32 from the anode strips.

The first and second plate bars 311, 312 project in the beam direction out of the housing 33 of the detector 3 and are each connected to a detection circuit 51, 52 at their ends. It is clear that the housing 33 of the detector 3 must be closed in order to be able to enclose the ionization gas and the quenching gas. For this purpose, a stopper 38 is incorporated between the plate bars 311, 312, connecting the two plate bars 311, 312 to one another in a gas-tight manner, for example by being glued to the plate bars 311, 312. The two plate bars 311, 312 in turn are connected to the wall of the housing 33 in a gas-tight manner, for example also by gluing.

As already mentioned, the anodes, as gold-plated copper strips in a grid of 400 $\mu$m, arranged on the sides of the plate bars 311, 312 facing one another project out of the housing 33 of the detector 3, and in particular in the form of 336 parallel strips which are arranged at a distance of about 0.3 mm and which each have a width of about 0.4 mm. The length of each plate bar 311, 312 is about 230 mm, while the length of the ionization chambers 31, 32 makes up about 60 mm.

Inside the ionization chambers 31, 32 the anode strips run parallel over a length of about 56 mm, while outside the ionization chambers 31, 32 they diverge, and in particular outside the housing 33 of the detector 3 are widened to a distance such that an electronic circuit 50, according to FIG. 3, can be connected to each anode strip in the detection circuit 51 and 52. In one embodiment the two detection circuits 51 and 52 thus comprise 2×336=672 electronic circuits 50, which have the structure shown in FIG. 3.

FIG. 3 shows one of the 2×336 electronic circuits 50, the input IN of which is connected to one of the 2×336 anode strips of the plate bars 311 or 312. The input IN of the electronic circuit 50 leads to the negative input of an operational amplifier OPA, the positive input of which is earthed. The operational amplifier OPA is a dielectrically-isolated FET of a type OPA 129 UB, produced by Burr-Brown. It is usually operated with ±15 V and is a very low-noise operational amplifier.

At the output of the operational amplifier OPA is connected a transistor T with its emitter, and in particular via a first resistance $R_1$ of 5.1 k$\Omega$. At the base of the transistor T lies a constant voltage source S which provides a direct voltage of −4 V. The collector of the transistor T lies at a point P which sees voltages from 0 to about 90 V during operation. For this reason the transistor T is a voltage-stable transistor which is employed as a base circuit. The collector of the transistor T couples back via the point P and a second resistance $R_2$ of 150 M$\Omega$ to the negative input of the operational amplifier OPA.

A high direct voltage of 100 V or more is applied to the point P of the electronic circuit 50, and in particular via a third resistance $R_3$ of, for example, 43 k$\Omega$.

The operational amplifier OPA keeps the differential voltage at its input to virtually zero volt, so that the current $i_s$ of the input signal flows via the resistance $R_2$ to the point P and from there via a fourth resistance $R_4$ of 30 M$\Omega$ to an analogue-digital converter ADC. The analogue-digital converter is a component of the type DDC 101 U from Burr-Brown with a resolution of 20 bits. This chip was designed specifically for reading out from photodiodes in which the positive charges or holes are read out. In its unipolar operation it can therefore be employed only for conversion of positive charge signals into 20 bit signals. The chip DDC 101 U can indeed also be employed in bipolar operation, but this reduces the output to 19 bits. In this operation, the noise of the chip is so high that it cannot be used for the present case of imaging.

For this reason only unipolar operation of the chip DDC 101 U is possible for the present application, although there is then the difficulty that the chip can process only positive charges (holes), while only negative charges, namely electrons, are delivered from the ionization chambers 31, 32 via the anode strips. It is therefore essential for the invention that positive charges which can be processed by the specific analogue-digital converter ADC of the DDC 101 U are made out of the negative charges which arrive at the input of the operational amplifier OPA. For this it is first necessary to make the resistance lying at the input of the analogue-digital converter $R_4$>20 M$\Omega$, since with resistances smaller than 20 M$\Omega$ the chip DDC 101 U generates a greater noise than the resistance noise, which is also called the Nyquist noise. However, if the noise already produces 4 bits, only 16 bits remain for the imaging, which is too few to achieve the required image resolution.

If, however, more than 20 M$\Omega$ is chosen for the resistance $R_4$, a correspondingly higher drive voltage is required at point P to charge the DDC 101 U up to 20 bits in about 0.2 msec. If 30 M$\Omega$, for example, is chosen for the resistance $R_4$, the control voltage at point P would have to be able to rise up to 90 volt or more. Such a high drive voltage can lead to destruction of the operational amplifier OPA, since it can tolerate only a maximum of 20 to 36 volt.

For this reason the voltage-stable transistor T is located in the base circuit between the operational amplifier OPA and the point P. As is known, the base circuit causes a voltage amplification, the transistor T being controlled to just such an extent that the voltage drop over the second resistance R ensures that the voltage difference at the input of the operational amplifier OPA is zero or virtually zero. The consequence of this is that the charges arriving at the operational amplifier OPA also arrive at the input of the analogue-digital converter, and in particular in five-fold amplification, since the resistance $R_2$ is chosen to be five times the resistance $R_4$. In a preferred embodiment, in fact, $R_2=150$ MΩ, $R_4=30$ MΩ.

The essence of the electronic circuit 50 according to the invention thus comprises the following measures:

1. Negative charges are converted into positive charges in order to be able to be processed by the chip DDC 101 U.
2. The drive voltage chosen for the ADC chip is up to 90 volt or more.
3. The high drive voltage for the ADC is held off from the operational amplifier by a base circuit.

A signal:noise ratio of 300,000:1 is achieved as a result, which is sufficient for the clarity of the image for the diagnosing doctor. The signal currents supplied to the anode strips from the ionization chambers 31, 32 moreover lie in the region of 100 fA or less, that is to say $i_{max}<100\times10^{-15}$ A. These currents are so low that they correspond to individual 33 keV photons.

What is claimed is:

1. Device for digital subtraction angiography in the energy subtraction mode,
   with a monochromator (1) for generating two monochromatic X-ray beams ($E_1$, $E_2$);
   with a safety system (8) with very rapid beam shutters;
   with a line scan device driven by a hydraulics system on which is mounted a stool (9) which can be moved up and down for positioning a patient;
   with a two-line detector (3);
   with a computer system (6) for control of the system, data acquisition and image processing; characterized
   in that the detector (3) is formed by two locally resolving ionization chambers (31, 32) which are filled with an ionization gas and have a certain number of anode strips (311, 312);
   in that a common drift cathode (313) is used for both ionization chambers (31, 32);
   in that to each ionization chamber (31, 32) is connected a separate detection circuit (51, 52) each with an electronic circuit (50) for each anode strip (311, 312), which operate linearly as a signal converter between 0 volt and 175 volt;
   in that each electronic circuit (50) has at its input an operational amplifier (OPA), to the negative input of which the input signal from the anode strips (311, 312) is applied, while the positive input is earthed;
   in that the output of the operational amplifier (OPA) is connected via a first resistance ($R_1$) to the emitter of a transistor (T) at the base of which lies a constant voltage source (S) and the collector of which is connected via a point (P) and a fourth resistance ($R_4$) to the input of an analogue/digital converter (ADC);
   in that the fourth resistance ($R_4$) is greater than 20 MΩ;
   in that a direct voltage is applied to the point (P) via a third resistance ($R_3$);
   in that a second resistance ($R_2$) which passes the input signal current ($i_s$) finally to the analogue/digital converter (ADC) lies between the input of the operational amplifier (OPA) and the point (P); and
   in that the outputs of all the electronic circuits (50) are transmitted as bit words via a bus system (511, 512) to the computer system (6).

2. Device according to claim 1, characterized in that the analogue/digital converter (ADC) is a 20 bit charge-digital converter.

3. Device according to claim 2, characterized in that the fourth resistance (R4) has 30 Mohm and the second resistance (R2) has 150 Mohm.

4. Device according to claim 1, characterized in that the first resistance ($R_1$) has 5.1 kohm and the third resistance ($R_3$) has 43 kohm.

5. Device according to claim 4, characterized in that about +145 V direct voltage lies at the side of the third resistance ($R_3$) facing away from point (P).

6. Device according to claim 5, characterized in that the transistor (T) operated as a base circuit is a transistor which is voltage-stable up to about 200 V.

7. Arrange according to claim 6, characterized in that the constant voltage source (S) applies a direct voltage of less than −1 V to the base of the transistor (T).

8. Device according to one of claims 1–7, characterized in that the operational amplifier (OPA) is formed by a dieiectrically-isolated FET circuit.

9. Device according to claim 1, characterized in that the detector (3) has a number of 336 signal leads for each energy ($E_1$, $E_2$).

10. Device for digital subtraction angiography in the energy subtraction mode,
    with a monochromator (1) for generating two monochromatic X-ray beams ($E_1$, $E_2$);
    with a safety system (8) with very rapid beam shutters;
    with a line scan device driven by a hydraulics system on which is mounted a stool (9) which can be moved up and down for positioning a patient;
    with a two-line detector (3);
    with a computer system (6) for control of the system, data acquisition and image processing; characterized
    in that the detector (3) is formed by two locally resolving ionization chambers (31, 32) which are filled with an ionization gas and have a certain number of anode strips (311, 312);
    in that a common drift cathode (313) is used for both ionization chambers (31, 32);
    in that to each ionization chamber (31, 32) is connected a separate detection circuit (51, 52) each with an electronic circuit (5) for each anode strip (311, 312), which operate linearly as a signal converter between 0 volt and 175 volt;
    in that each electronic circuit (50) has at its input an operational amplifier (OPA), to the negative input of which the input signal from the anode strips (311, 312) is applied, while the positive input is earthed;
    in that the output of the operational amplifier (OPA) is connected via a first resistance ($R_1$) to the emitter of a transistor (T) at the base of which lies a constant voltage source (S) and the collector of which is connected via a point (P) and a fourth resistance ($R_4$) to the input of an analogue/digital converter (ADC);
    in that the fourth resistance ($R_4$) is greater than 20 MΩ;
    in that a second resistance ($R_2$) which passes the input signal current ($i_s$) finally to the analogue/digital converter (ADC) lies between the input of the operational amplifier (OPA) and the point (P);

in that the outputs of all the electronic circuits (50) are transmitted as bit words via a bus system (511, 512) to the computer system (6); and in that the fourth resistance ($R_4$) has 30 Mohm and the second resistance ($R_2$) has 150 Mohm.

11. Device according to claim 10, characterized in that the transistor (T) operated as a base circuit is a transistor which is voltage-stable up to about 200 V.

12. Device according to claim 11, characterized in that the constant voltage source (S) applies a direct voltage of less than −1 V to the base of the transistor (T).

13. Device according to claim 12, characterized in that the operational amplifier (OPA) is formed by a dieleotrically-isolated FET circuit.

14. Device for digital subtraction angiography in the energy subtraction mode, with a monochromator (1) for generating two monochromatic X-ray beams ($E_1$, $E_2$)

with a safety system (8) with very rapid beam shutters;

with a line scan device driven by a hydraulics system on which is mounted a stool (9) which can be moved up and down for positioning a patient;

with a two-line detector (3);

with a computer system (6) for control of the system, data acquisition and image processing; characterized in that the detector (3) is formed by two locally resolving ionization chambers (31, 32) which are filled with an ionization gas and have a certain number of anode strips (311, 312);

in that a common drift cathode (313) is used for both ionization chambers (31, 32);

in that to each ionization chamber (31, 32) is connected a separate detection circuit (51, 52) each with an electronic circuit (5) for each anode strip (311, 312), which operate linearly as a signal converter between 0 volt and 175 volt;

in that each electronic circuit (50) has at its input an operational amplifier (OPA), to the negative input of which the input signal from the anode strips (311, 312) is applied, while the positive input is earthed;

in that the output of the operational amplifier (OPA) is connected via a first resistance ($R_1$) to the emitter of a transistor (T) at the base of which lies a constant voltage source (S) and the collector of which is connected via a point (P) and a fourth resistance ($R_4$) to the input of an analogue/digital converter (ADC);

in that the fourth resistance ($R_4$) is greater than 20 MΩ;

in that a second resistance ($R_2$) which passes the input signal current ($i_s$) finally to the analogue/digital converter (ADC) lies between the input of the operational amplifier (OPA) and the point (P);

in that the outputs of all the electronic circuits (50) are transmitted as bit words via a bus system (511, 512) to the computer system (6);

in that the analogue/digital converter (ADC) is a 20 bit charge-digital converter; and in that the transistor (T) operated as a base circuit is a transistor which is voltage-stable up to about 200 V.

* * * * *